United States Patent [19]

Purkaystha et al.

[11] Patent Number: 5,002,771

[45] Date of Patent: Mar. 26, 1991

[54] CALCITONIN SUPPOSITORY FORMULATIONS

[75] Inventors: Abdur R. Purkaystha, Horsham; Gary G. Gazdick, Wyndmoor; Jay E. Dorrell, Wayne; Keith C. Mozzone, Jeffersonville; Howard J. Levin, Norristown, all of Pa.

[73] Assignee: Rorer Pharmaceutical Corp., Fort Washington, Pa.

[21] Appl. No.: 306,696

[22] Filed: Feb. 3, 1989

[51] Int. Cl.$^5$ .............................................. A61F 13/00
[52] U.S. Cl. .............................. 424/433; 424/DIG. 5; 530/307
[58] Field of Search ...................... 424/433, DIG. 15; 530/307

[56] References Cited

U.S. PATENT DOCUMENTS

| | | | |
|---|---|---|---|
| 4,434,159 | 2/1984 | Sekine et al. | 514/808 |
| 4,597,900 | 7/1986 | Orlowski et al. | 530/307 |
| 4,609,640 | 9/1986 | Morishita | 530/350 |
| 4,746,728 | 5/1988 | Orlowski et al. | 530/307 |

Primary Examiner—Merrell C. Cashion, Jr.
Assistant Examiner—P. L. Prater

[57] ABSTRACT

Disclosed are rectal and vaginal suppository formulations comprising calcitonin and caprylic acid monoglyceride in a pharmaceutically acceptable suppository vehicle.

39 Claims, No Drawings

CALCITONIN SUPPOSITORY FORMULATIONS

BACKGROUND OF THE INVENTION

1. Field of the Invention

The present invention relates to a novel method of administering calcitonin to patients and to formulations adapted for rectal and vaginal administration. More particularly, the present invention relates to calcitonin-containing pharmaceutical formulations containing therein caprylic acid monoglyceride which promotes absorption of calcitonin and thereby enhances its bioavailability.

2. Description of the Prior Art

The method of administration of pharmaceutically active calcitonin is predominantly by injection, although efforts were made in the prior art to use other modes of administration. While administration by injection is acceptable for short-term therapy, administration by injection to patients in need of long-term calcitonin therapy has serious problems. Not only is it costly to patients to have physicians do the administration for extended periods of time, but it is also painful and inconvenient. Nor can calcitonin be given orally to patients since oral administration will result in degradation of calcitonin.

Recently, the prior art has found that calcitonin may also be administered via the rectal route; however, it was also found that certain absorption promoters enhance absorption of calcitonin through the rectal mucosa and as such may be used to advantage in calcitonin suppositories. Absorption promoters that provided increased absorption include certain surface active agents, amino acid derivatives, and certain nonsurfactant adjuvenants, such as, ethylacetoacetate, dimethylethoxymethylenemalonate, sodium salicylate and the like.

SUMMARY OF THE INVENTION

This invention relates to a suppository formulation comprising: from about 0.0004% w/w to about 0.20% w/w, and preferably from about 0.005% w/w to about 0.05% w/w of calcitonin having a potency of about 25 to 6,000 IU/mg of peptide or higher as hereinafter defined; from about 2.5% w/w to about 50.0% w/w and preferably from about 10% w/w to about 40% w/w of caprylic acid monoglyceride and a pharmaceutically acceptable suppository vehicle. The invention also relates to a method for increasing the absorption of calcitonin through the rectal and/or vaginal mucosa by utilizing caprylic acid monoglyceride in the suppository formulations. Hereinafter the invention will be described with reference to rectal administration; however, it is to be noted that, vaginal administration is intended to be covered as well.

According to the invention, there is also provided a method for the treatment of human patients suffering from diseases of hyperparathyroidism, idiopathic hypercalcemia of infancy, Paget's disease, vitamin D intoxication, or osteolytic bone metastases. Said diseases are characterized by hypercalcemia and high phosphate concentrations and their treatment is effected by decreasing serum calcium and phosphate concentrations in the blood by rectal application of a calcitonin containing composition to effect control of said diseases by transmucosal action.

The term calcitonin as used herein means not only polypeptides having a structure corresponding to one of the naturally occurring hormones, and which may be naturally or synthetically produced, but also analogs thereof and related synthetic peptides having calcitonin activity.

DETAILED DESCRIPTION OF THE INVENTION

In accordance with the present invention, suppository pharmaceutical formulations are provided in which caprylic acid monoglyceride is incorporated for enhancing the absorption of calcitonin through the rectal mucosa. The composition of the formulations are described hereunder.

Calcitonin

Calcitonin is a polypeptide hormone involved in the control of calcium metabolism in the body. All known natural calcitonin peptides contain an amino acid sequence of 32 amino acids, of which the seven at the amino terminal end of the peptide chain are held in a cyclic configuration by a sulphur or carbon bridge and the carboxyl terminal residue consists of proline amide. The natural calcitonins include the salmon, eel, bovin, porcine, ovine, rat and human calcitonins. The detailed structure within the peptide chain of the hormone varies among different species and while the hormones, and their derivatives and analogues found in various species are of interest for use in the present invention, salmon calcitonin is of special interest in view of its relatively hydrophobic character and its stability. Salmon calcitonin has the following formula:

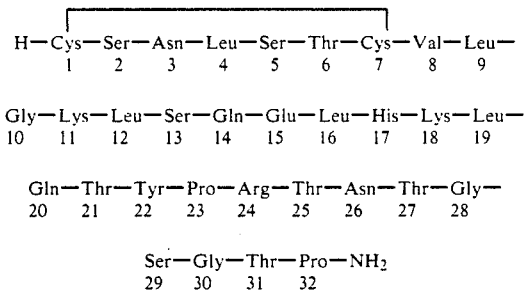

In U.S. Pat. Nos. 3,926,938, 4,062,815, 3,929,758, 4,033,940, 4,336,187, 4,388,235, 4,391,747 and 4,401,593 are disclosed improved synthesis of calcitonins including the salmon calcitonin referred to above.

Human, salmon and porcine calcitonins have been available for therapeutic use for several years. For example, synthetic salmon calcitonin is marketed by Armour Pharmaceutical Co. under the tradename CALCIMAR in a sterile, lyophilized form reconstitutable for subcutaneous or intravascular injection for the treatment of bone diseases.

The level of hypocalcemic activity of calcitonins varies from species to species Salmon and chicken calcitonin have a potency of about 4,000 to 6,000 MCR (Medical Research Council) U/mg peptide; eel calcitonin about 2,000 to 4,000 MRC U/mg peptide; rat 400 MRC U/mg; while beef, sheep, hog and man about 100 to 200 MRC U/mg peptide.

Calcitonin used by the present invention may be obtained from Armour Pharmaceutical Co., from natural sources, or by synthetic routes known in the art. The synthesis can be performed by classical peptide synthesis as well as by solid phase synthesis.

In addition to the above-described calcitonins, the present invention encompasses synthetic calcitonin peptides having biological activity of the same type as those above-described Such synthetic calcitonins are disclosed, along with processes for preparation thereof in the following U.S. Pat. Nos.

| | |
|---|---|
| 4,388,235 | 4,604,238 |
| 4,391,747 | 4,605,514 |
| 4,397,780 | 4,605,515 |
| 4,401,593 | 4,606,856 |
| 4,414,149 | 4,622,386 |
| 4,444,681 | 4,622,387 |
| 4,451,395 | 4,622,388 |
| 4,469,636 | 4,632,978 |
| 4,497,731 | 4,639,509 |
| 4,497,732 | 4,639,510 |
| 4,528,132 | 4,639,511 |
| 4,537,716 | 4,650,854 |
| 4,597,900 | 4,659,804 |
| 4,604,236 | 4,732,969 |
| 4,604,237 | 4,746,728 |

Synthetic calcitonin analogues disclosed in these patents are incorporated herein by reference as if set out in full herein. This list is not intended to be exhaustive of all U.S. Patents covering synthetic calcitonin analogues, but is representative of the analogues useful in the present invention; nor is the invention limited to the compounds disclosed in the listed patents.

In accordance for the foregoing, the following analogues of calcitonin constitute specific active ingredients used in the various suppository formulations of the present invention:

1. Des Asparagine-3-Calcitonins having the structures:

(a) H—Cys—Ser—Leu—Ser—Thr—Cys—Val—Leu—Gly—Lys—Leu—Ser—Gln—Glu—Leu—His—Lys—Leu—Gln—Thr—Tyr—Pro—Arg—Thr—Asn—Thr—Gly—Ser—Gly—Thr—Pro—NH$_2$; and (b) Cys—Ser—Leu—Ser—Thr—Cys—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH$_2$.

2. [16-Alanine] Calcitonins having the following structures:

(a) Cys—Ser—Asn—Leu—Ser—Thr—Cys—Val—Leu—Gly—Lys—Leu—Ser—Gln—Glu—Ala—His—Lys—Leu—Gln—Thr—Tyr—Pro—Arg—Thr—Asn—Thr—Gly—Ser—Gly—Thr—Pro—NH$_2$ (Salamon);

(b) Cys—Ser—Asn—Leu—Ser—Thr—Cys—Val—Leu—Gly—Lys—Leu—Ser—Gln—Glu—Ala—His—Lys—Leu—Gln—Thr—Tyr—Pro—Arg—Thr—Asp—Val—Gly—Ala—Gly—Thr—Pro—NH$_2$ (Eel); and (c) Cys—Gly—Asn—Leu—Ser—Thr—Cys—Met—Leu—Gly—Thr—Tyr—Thr—Gln—Asp—Ala—Asn—Lys—Phe—His—Thr—Phe—Pro—Gln—Thr—Ala—Ile—Gly—Val—Gly—Ala—Pro—NH$_2$ (Human).

3. Des $^2$-glycine $^8$-Des $^{22}$-Calcitonins having the structures:

(a) H—Cys—Asn—Leu—Ser—Thr—Cys—Gly—Leu—Gly—Lys—Leu—Ser—Gln—Glu—Leu—His—Lys—Leu—Gln—Thr—Pro—Arg—Thr—Asn—Thr—Gly—Ser—Gly—Thr—Pro—NH$_2$ (Salmon); and (b) H—Cys—Asn—Leu—Ser—Thr—Cys—Gly—Leu—Gly—Lys—Leu—Ser—Gln—Glu—Leu—His—Lys—Leu—Gln—Thr—Pro—Arg—Thr—Asp—Val—Gly—Ala—Gly—Thr—Pro—Nh$_2$ (Eel).

4. Des-13-Serine-Calcitonins having the following structures:

(a) Cys—Ser—Asn—Leu—Ser—Thr—Cys—Val—Leu—Gly—Lys—Leu—Gln—Glu—Leu—His—Lys—Leu—Gln—Thr—Tyr—Pro—Arg—Thr—Asn—Thr—Gly—Ser—Gly—Thr—Pro—NH$_2$;

(b) Cys—Ser—Asn—Leu—Ser—Thr—Cys—Val—Leu—Gly—Lys—Leu—Gln—Glu—Leu—His—Lys—Leu—Gln—Thr—Tyr—Pro—Arg—Thr—Asp—Val—Gly—Ala—Gly—Thr—Pro—NH$_2$; and (c) Cys—Gly—Asn—Leu—Ser—Thr—Cys—Met—Leu—Gly—Thr—Tyr—Gln—Asp—Phe—Asn—Lys—Phe—His—The—Phe—Pro—Gln—Thr—Ala—Ile—Gly—Val—Gly—Ala—Pro—NH$_2$.

5. Des-21-Threonine-Calcitonins having the following structures:

(a) Cys—Ser—Asn—Leu—Ser—Thr—Cys—Val—Leu—Gly—Lys—Leu—Ser—Gln—Glu—Leu—His—Lys—Leu—Gln—Tyr—Pro—Arg—Thr—Asn—Thr—Gly—Ser—Gly—Thr—Pro—NH$_2$ (Salmon);

(b) Cys—Ser—Asn—Leu—Ser—Thr—Cys—Val—Leu—Gly—Lys—Leu—Ser—Gln—Glu—Leu—His—Lys—Leu—Gln—Tyr—Pro—Arg—Thr—Asp—Val—Gly—Ala—Gly—Thr—Pro—NH$_2$, (Eel); and (c) Cys—Gly—Asn—Leu—Ser—Thr—Cys—Met—Leu—Gly—Thr—Tyr—Thr—Gln—Asp—Phe—Asn—Lys—Phe—His—Phe—Pro—Gln—Thr—Ala—Ile—Gly—Val—Gly—Ala—Pro—NH$_2$ (Human).

6. [Gly$^2$, Ser$^3$, des-Tyr$^{22}$] calcitonins having the following structures:

(a) Cys—Gly—Ser—Leu—Ser—Thr—Cys—Gly—Leu—Gly—
    Lys—Leu—Ser—Gln—Glu—Leu—His—Lys—Leu—
    Gln—Thr—Pro—Arg—Thr—Asn—Thr—Gly—Ser—
    Gly—Thr—Pro—NH₂; and (b) Cys—Gly—Ser—Leu—Ser—Thr—Cys—Gly—Lue—Gly—
    Lys—Leu—Ser—Gln—Glu—Leu—His—Lys—Leu—
    Gln—Thr—Pro—Arg—Thr—Asp—Val—Gly—Ala—
    Gly—Thr—Pro—NH₂.

7. Des-4-Leucine-Calcitonins having the following structures:

(a) Cys—Ser—Asn—Ser—Thr—Cys—Val—Leu—Gly—Lys—Leu—
    Ser—Gln—Glu—Leu—His—Lys—Leu—Gln—Thr—Tyr—
    Pro—Arg—Thr—Asn—Thr—Gly—Ser—Gly—Thr—Pro—
    NH₂ (Salmon);

(b) Cys—Ser—Asn—Ser—Thr—Cys—Val—Leu—Gly—Lys—Leu—
    Ser—Gln—Glu—Leu—His—Lys—Leu—Gln—Thr—Tyr—
    Pro—Arg—Thr—Asp—Val—Gly—Ala—Gly—Thr—Pro—
    NH₂ (Eel); and (c) Cys—Gly—Asn—Ser—Thr—Cys—Met—Leu—Gly—Thr—Tyr—
    Thr—Gln—Asp—Phe—Asn—Lys—Phe—His—Thr—Phe—
    Pro—Gln—Thr—Ala—Ile—Gly—Val—Gly—Ala—Pro—
    NH₂ (Human).

8. Calcitonin-(1-23)-Peptide Amides having the following structures:

(a) Cys—Ser—Asn—Leu—Ser—Thr—Cys—Val—Leu—Gly—
    Lys—Leu—Ser—Gln—Glu—Leu—His—Lys—Leu—
    Gln—Thr—Tyr—Pro—NH₂; and (b) Cys—Ser—Asn—Leu—Ser—Thr—Cys—Val—Leu—Gly—
    $R_1$ (above first Cys), $R_2$ (above second Cys)
    Lys—Leu—Ser—Gln—Glu—Leu—His—Lys—Leu—Gln—
    Thr—Tyr—Pro—NH₂.

9. [Des-1-Amino,8-Glycine) Calcitonins having the following structures:

(a) Bmp—Ser—Asn—Leu—Ser—Thr—Cys—Gly—Leu—Gly—
    Lys—Leu—Ser—Gln—Glu—Leu—His—Lys—Leu—Gln—
    Thr—Tyr—Pro—Arg—Thr—Asn—Thr—Gly—Ser—Gly—
    Thr—Pro—NH₂ (Salmon); and (b) Bmp—Ser—Asn—Leu—Ser—Thr—Cys—Val—Leu—Gly—
    Lys—Leu—Ser—Gln—Glu—Leu—His—Lys—Leu—Gln—
    Thr—Tyr—Pro—Arg—Thr—Asp—Val—Gly—Ala—Gly—
    Thr—Pro—NH₂ (Eel).

10. [1,7-Di-Alanine] Calcitonins having the following structures:

(a) Ala—Ser—Asn—Leu—Ser—Thr—Ala—Val—Leu—Gly—Lys—
    Leu—Ser—Gln—Glu—Ala—His—Lys—Leu—Gln—Thr—Tyr—
    Pro—Arg—Thr—Asn—Thr—Gly—Ser—Gly—Thr—Pro—NH₂; and (b) Ala—Ser—Asn—Leu—Ser—Thr—Ala—Val—Leu—Gly—Lys—
    Leu—Ser—Gln—Glu—Ala—His—Lys—Leu—Gln—Thr—
    Tyr—Pro—Arg—Thr—Asp—Val—Gly—Ala—
    Gly—Thr—Pro—NH₂.

11. 8-Methionine Calcitonins having the following structures:

(a) Cys—Ser—Asn—Leu—Ser—Thr—Cys—Met—Leu—
    Gly—Lys—Leu—Ser—Gln—Glu—Leu—His—Lys—
    Leu—Gln—Thr—Tyr—Pro—Arg—Thr—Asn—Thr—
    Gly—Ser—Gly—Thr—Pro—NH₂; and (b) Cys—Ser—Asn—Leu—Ser—Thr—Cys—Met—Leu—
    Gly—Lys—Leu—Ser—Gln—Glu—Leu—His—Lys—
    Leu—Gln—Thr—Tyr—Pro—Arg—Thr—Asp—Val—
    Gly—Ala—Gly—Thr—Pro—NH₂.

12. Des-2-Serine, 3-Asparagine Calcitonins having the following structures:

(a) Cys—Leu—Ser—Thr—Cys—Val—Leu—Gly—Lys—
    Leu—Ser—Gln—Glu—Leu—His—Lys—Leu—Gln—
    Thr—Tyr—Pro—Arg—Thr—Asn—Thr—Gly—Ser—
    Gly—Thr—Pro—NH₂; and (b) Cys—Leu—Ser—Thr—Cys—Val—Leu—Gly—Lys—
    Leu—Ser—Gln—Glu—Leu—His—Lys—Leu—Gln—
    Thr—Tyr—Pro—Arg—Thr—Asp—Val—Gly—Ala—
    Gly—Thr—Pro—NH₂.

13. G-Serine, Des-19-Leucine Calcitonins having the following structures:

(a) Cys—Ser—Asn—Leu—Ser—Ser—Cys—Val—Leu—Gly—
    Lys—Leu—Ser—Gln—Glu—Leu—His—Lys—Gln—Thr—
    Tyr—Pro—Arg—Thr—Asn—Thr—Gly—Ser—

-continued

Gly—Thr—Pro—NH$_2$; and (b) ⌐Cys—Ser—Asn—Leu—Ser—Ser—Cys⌐—Val—Leu—
    Gly—Lys—Leu—Ser—Gln—Glu—Leu—His—Lys—Gln—
    Thr—Tyr—Pro—Arg—Thr—Asp—Val—Gly—Ala—Gly—
    Thr—Pro—NH$_2$.

14. [16,19-Di-Alanine] Calcitonins having the following structures:

(a) ⌐Cys—Ser—Asn—Leu—Ser—Thr—Cys⌐—Val—Leu—Gly—
    Lys—Leu—Ser—Gln—Glu—Ala—His—Lys—Ala—Gln—
    Thr—Tyr—Pro—Arg—Thr—Asn—Thr—Gly—Ser—Gly—
    Thr—Pro—NH$_2$; and (b) ⌐Cys—Ser—Asn—Leu—Ser—Thr—Cys⌐—Val—Leu—Gly—
    Lys—Leu—Ser—Gln—Glu—Ala—His—Lys—Ala—Gln—
    Thr—Tyr—Pro—Arg—Thr—Asp—Val—Gly—Ala—Gly—
    Thr—Pro—NH$_2$.

15. (1-S-Acetamidomethyl Custeine, 7-Alanine) Calcitonins having the following structures:

(a) SCH$_2$NH—C(O)—CH$_3$
    |
    Cys—Ser—Asn—Leu—Ser—Thr—Ala—Val—Leu—Gly—
    Lys—Leu—Ser—Gln—Glu—Leu—His—Lys—Leu—Gln—
    Thr—Tyr—Pro—Arg—Thr—Asn—Thr—Gly—Ser—Gly—
    Thr—Pro—NH$_2$; and (b) SCH$_2$NH—C(O)—CH$_3$
    |
    Cys—Ser—Asn—Leu—Ser—Thr—Ala—Val—Leu—Gly—
    Lys—Leu—Ser—Gln—Glu—Leu—His—Lys—Leu—Gln—
    Thr—Tyr—Pro—Arg—Thr—Asp—Val—Gly—Ala—Gly—
    Thr—Pro—NH$_2$.

16. Des-19-Leucine - Calcitonin Analogs having the following structures:

(a) ⌐Cys—Ser—Asn—Leu—Ser—Thr—Cys⌐—Val—Leu—
    Gly—Lys—Leu—Ser—Gln—Glu—Leu—His—Lys—
    Gln—Thr—Tyr—Pro—Arg—Thr—Asn—Thr—Gly—
    Ser—Gly—Thr—Pro—NH$_2$; and (b) ⌐Cys—Ser—Asn—Leu—Ser—Thr—Cys⌐—Val—Leu—
    Gly—Lys—Leu—Ser—Gln—Glu—Leu—His—Lys—
    Gln—Thr—Tyr—Pro—Arg—Thr—Asp—Val—Gly—
    Ala—Gly—Thr—Pro—NH$_2$.

17. (Bis-1,7-S-Acetamidomethyl-L-Cysteine) Salmon Calcitonins having the following structures:

(a) 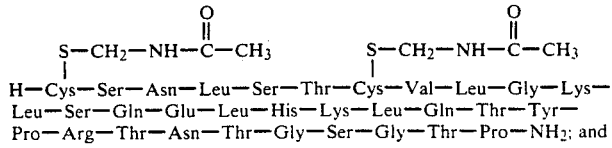
H—Cys—Ser—Asn—Leu—Ser—Thr—Cys—Val—Leu—Gly—Lys—
Leu—Ser—Gln—Glu—Leu—His—Lys—Leu—Gln—Thr—Tyr—
Pro—Arg—Thr—Asn—Thr—Gly—Ser—Gly—Thr—Pro—NH$_2$; and (b) 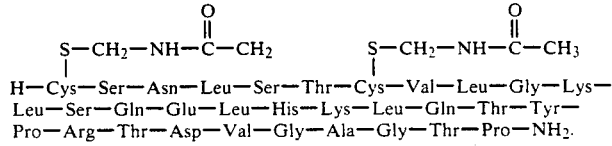
H—Cys—Ser—Asn—Leu—Ser—Thr—Cys—Val—Leu—Gly—Lys—
Leu—Ser—Gln—Glu—Leu—His—Lys—Leu—Gln—Thr—Tyr—
Pro—Arg—Thr—Asp—Val—Gly—Ala—Gly—Thr—Pro—NH$_2$.

18. 8-Glycine, Des-19-Leucine-Calcitonins having the following structures:

(a) ⌐Cys—Ser—Asn—Leu—Ser—Thr—Cys⌐—Gly—Leu—Gly—
    Lys—Leu—Ser—Gln—Glu—Leu—His—Lys—Gln—
    Thr—Tyr—Pro—Arg—Thr—Asn—Thr—Gly—Ser—
    Gly—Thr—Pro—NH$_2$ (Salmon);

(b) ⌐Cys—Ser—Asn—Leu—Ser—Thr—Cys⌐—Gly—Leu—Gly—
    Lys—Leu—Ser—Gln—Glu—Leu—His—Lys—Gln—
    Thr—Tyr—Pro—Arg—Thr—Asp—Val—Gly—Ala—
    Gly—Thr—Pro—NH$_2$ (Eel); and (c) ⌐Cys—Ala—Ser—Leu—Ser—Thr—Cys⌐—Gly—Leu—Gly—
    Lys—Leu—Ser—Gln—Glu—Leu—His—Lys—Gln—
    Thr—Tyr—Pro—Arg—Thr—Asp—Val—Gly—Ala—
    Gly—Thr—Pro—NH$_2$ (Chicken).

19. Des-Leu[16]-Calcitonins having the following structures:

(a) ⌐Cys—Ser—Asn—Leu—Ser—Thr—Cys⌐—Val—Leu—Gly—
    Lys—Leu—Ser—Gln—Glu—His—Lys—Leu—Gln—
    Thr—Tyr—Pro—Arg—Thr—Asn—Thr—Gly—Ser—
    Gly—Thr—Pro—NH$_2$ (Salmon);

(b) ⌐Cys—Ser—Asn—Leu—Ser—Thr—Cys⌐—Val—Leu—Gly—
    Lys—Leu—Ser—Gln—Glu—His—Lys—Leu—Gln—
    Thr—Tyr—Pro—Arg—Thr—Asp—Val—Gly—Ala—
    Gly—Thr—Pro—NH$_2$ (Eel); and (c) ⌐Cys—Gly—Asn—Leu—Ser—Thr—Cys⌐—Met—Leu—Gly—
    Thr—Tyr—Thr—Gln—Asp—Asn—Lys—Phe—His—
    Thr—Phe—Pro—Glu—Thr—Ala—Ile—Gly—Val—
    Gly—Ala—Pro—NH$_2$ (Human).

20. Leucine[22] - Calcitonins having the following structures:

(a) H—⌐Cys—Ser—Asn—Leu—Ser—Thr—Cys⌐—Val—Leu—Gly—
    Lys—Leu—Ser—Gln—Glu—Leu—His—Lys—Leu—Gln—Thr—
    Leu—Pro—Arg—Thr—Asn—Thr—Gly—Ser—Gly—Thr—Pro—

NH₂ (Salmon); and (b) H—Cys—Ser—Asn—Leu—Ser—Thr—Cys—Val—Leu—Gly—Lys—
Leu—Ser—Gln—Glu—Leu—His—Lys—Leu—Gln—Thr—Leu—Pro—
Arg—Thr—Asp—Val—Gly—Ala—Gly—Thr—Pro—NH₂ (Eel).

21. Glycine - 8 Calcitonins having the following structures:

(a) H—Cys—Ser—Asn—Leu—Ser—Thr—Cys—Gly—Leu—Gly—Lys—
Leu—Ser—Gln—Glu—Leu—His—Lys—Leu—Gln—Thr—Tyr—
Pro—Arg—Thr—Asn—Thr—Gly—Ser—Gly—Thr—Pro—NH₂; and (b) Cys—Gly—Asn—Leu—Ser—Thr—Cys—Gly—Leu—Gly—Thr—
Tyr—Thr—Gln—Asp—Phe—Asn—Lys—Phe—His—Thr—Phe—Pro—
Gln—Thr—Ala—Ile—Gly—Val—Gly—Ala—Pro—NH₂.

22. Glycine⁸-D-Arginine²⁴ Calcitonins having the following structures:

(a) H—Cys—Ser—Asn—Leu—Ser—Thr—Cys—Gly—Leu—
Gly—Lys—Leu—Ser—Gln—Glu—Leu—His—Lys—
Leu—Gln—Thr—Tyr—Pro—D—Arg—Thr—Asn—Thr—
Gly—Ser—Gly—Thr—Pro—NH₂ (Salmon); and (b) H—Cys—Ser—Asn—Leu—Ser—Thr—Cys—Gly—Leu—
Gly—Lys—Leu—Ser—Gln—Glu—Leu—His—Lys—
Leu—Gln—Thr—Tyr—Pro—D—Arg—Thr—Asp—Val—
Gly—Ala—Gly—Thr—Pro—NH₂ (Eel).

23. L-Tyrosine²¹ Calcitonins having the following structures:

(a) H—Cys—Ser—Asn—Leu—Ser—Thr—Cys—Val—Leu—
Gly—Lys—Leu—Ser—Gln—Glu—Leu—His—Lys—
Leu—Gln—Tyr—Tyr—Pro—Arg—Thr—Asn—Thr—
Gly—Ser—Gly—Thr—Pro—NH₂ (Salmon); and (b) H—Cys—Ser—Asn—Leu—Ser—Thr—Cys—Val—Leu—
Gly—Lys—Leu—Ser—Gln—Glu—Leu—His—Lys—
Leu—Gln—Tyr—Tyr—Pro—Arg—Thr—Asp—Val—
Gly—Ala—Gly—Thr—Pro—NH₂ (Eel).

24. D-Arginine²⁴ Calcitonins having the following structures:

(a) H—Cys—Ser—Asn—Leu—Ser—Thr—Cys—Val—Leu—
Gly—Lys—Leu—Ser—Gln—Glu—Leu—His—Lys—
Leu—Gln—Thr—Tyr—Pro—D—Arg—Thr—Asn—Thr—
Gly—Ser—Gly—Thr—Pro—NH₂ (Salmon); and (b) H—Cys—Ser—Asn—Leu—Ser—Thr—Cys—Val—Leu—
Gly—Lys—Leu—Ser—Gln—Glu—Leu—His—Lys—
Leu—Gln—Thr—Tyr—Pro—D—Arg—Thr—Asp—Val—
Gly—Ala—Gly—Thr—Pro—NH₂ (Eel).

25. Amides Analogues of Calcitonin having the following structures:

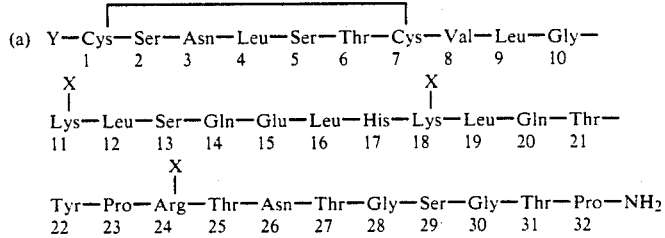

wherein Y is N(a) decanoyl and X is N(e) decanoyl.

26. [N-alpha, 1,7-Di-Alanine, Des-19-Leucine] Calcitonins having the following structures:
(a) [N-alpha-X, 1, 7 Di-Alanine (8-Y) Des-19-Leucine] calcitonins, wherein X is H, free amino or acyl-amino wherein acyl is derived from a carboxylic acid having 1–10 carbon atoms, L-lactic acid or half amide of malonic, succinic, glutaric, or adipic acids; Y is L-valine, glycine, L-methionine, L-alanine, L-leucine or L-isoleucine; and
(b) [N-alpha-X, 1, 7-Di-Alanine, Des-19-Leucine] calcitonins, wherein X is an acyl derived from carboxylic acid having 1-5 carbon atoms.

27. 1,7-Di-Alanine, 8-Glycine, Des-19-Leucine Calcitonin having the following structure:

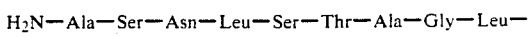
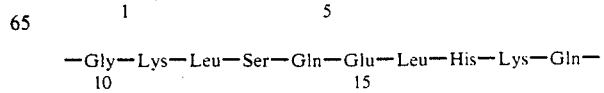

-continued

—Thr—Tyr—Pro—Arg—Thr—Asn—Thr—Gly—Ser—Gly—
20                                        25

—Thr—Pro—(C=O)—NH$_2$.
30

28 Nα-Propionyl, 1,7-Di-Alanine, Des-19-Leucine Calcitonin having the following structure:

CH$_3$—CH$_2$—(C=O)-Hn-
Ala—Ser—Asn—Leu—Ser—Thr—Ala—Val—Leu—
1                      5

—Gly—Lys—Leu—Ser—Gln—Glu—Leu—His—Lys—Gln—
10                                       15

—Thr—Tyr—Pro—Arg—Thr—Asn—Thr—Gly—Ser—Gly—
20                                        25

—Thr—Pro—(C=O)—NH$_2$.
30

Caprylic Acid Monoglyceride

Absorption of calcitonin through the rectal mucosa is enhanced by the presence of caprylic acid monoglyceride in the formulations of the present invention. Caprylic acid monoglyceride or glyceryl caprylate may be obtained by using a state-of-the-art method of preparation, or it may be obtained from commercial suppliers, such as Dynamit Nobel under the tradename Imwitor 308, which contains a mixture of mono-, di- and triglycerides of caprylic acid with a typical ratio of 60:30:10. As used in connection with the specification and claims of the present invention, the term caprylic acid monoglyceride will be used to denote the commercially supplied mixture of mono-, di-and triglycerides of caprylic acid.

The Suppository Vehicle

The biologically/pharmacologically active calcitonin, as hereinbefore defined, and caprylic acid monoglyceride are formulated with a suppository vehicle adapted for rectal administration.

The suppository vehicle comprises a suppository base and certain adjuvenants and additives suitable for making such, formulations. The suppository base may be an aqueous or a fatty base material, the latter being preferred mainly for ease of formulation and administration. The fatty base material for use in the present invention includes: fatty oils and fats, such as cocoa butter, palm oil, coconut oil, lard; waxes, such as lanolin and vasoline; fatty acids, such as, oleic-, stearic-, and lauric acids. We prefer to use a suppository base consisting essentially of polyethylene glycols or mixtures of mono-, di-, and triglycerides of fatty acids of $C_{10}$ to $C_{20}$ chain length. These are obtainable as polyethylene glycol 1,000–8,000 (PEG=polymer of ethylene oxide, mol. wt. 1,000–8,000); cocoa butter, NF (fat obtained from the roasted seed of Theobroma cacao); Suppocire AIX (semi-synthetic glycerides with ethoxylated fatty acid esters containing 95% mono-, di- and triglycerides and 5% polysorbate 65); Witepsol S 55 (semi-synthetic glycerides with ethoxylated fatty acid esters containing 98% mono-, di- and triglycerides and 2% PEG25 - cetyl stearyl alcohol) and Witepsol E75, supplied by Dynamit Nobel, which is glyceryl esters of saturated fatty acids of chain length $C_{10}$–$C_{18}$.

The preparations of the present invention may also contain other additives, such as antioxidants, stabilizers, viscosity builders, preservatives, and the like. The concentration of these additives may vary according to the particular additive used and the desired result sought The use of the kind and concentration of additives are well within the ability of the skilled artisan.

We contemplate three methods by which calcitonin can be incorporated into the suppository system, namely, by the use of: (1) a buffer system, (2) a gelatin stabilizer and (3) a bulking agent.

(1) According to this method, a buffer system is used as a carrier for the calcitonin which provides stability for the same and facilitates its admixture with the suppository vehicle.

The buffer system of the present invention preferably contains a sodium or potassium phosphate/phosphoric acid buffer or a sodium or potassium acetate/acetic acid buffer or a sodium or potassium citrate/citric acid buffer in the range of 0.01 M to 0.5M and preferably in the range of 0.05 M to 0.2 M. The pH range of these buffers are between 2 0 to 8.0. This concentration was found effective to provide stability of the dissolved calcitonin in the vehicle.

(2) According to this method, the stabilizer system contains from about 1 to about 32% w/w of a gelatin hydrolized in a 0.9% w/w sodium chloride solution or in purified water. The pH range of the stabilizer system is between 2.0 to 8.0. This stabilizer system has been found very effective in providing stability to the dissolved calcitonin.

(3) According to this method, a lyophilized or dry mixed bulking agent is used as a carrier for calcitonin. The ratio of calcitonin to the bulking powder is about 10 to 60,000 IU per mg. Examples of bulking agents include, but are not limited to, gelatin, methionine, dextrose, sucrose, mannitol, sorbitol, lactose, methyl cellulose, povidone, sodium chloride and sodium acetate.

Preparation of the Formulations

In general the preparation of the formulations of the present invention is as follows: the absorption promoter is melted with the suppository base; antioxidants, such as BHA (bttylated hydroxyanisole, USP) and BHT (butylated hydroxytoluene, USP) are added thereto and dissolved thereby forming the suppository vehicle; calcitonin is dissolved in a buffer solution or a stabilizer system or homogenously distributed in a bulk powder mix and is blended with the suppository vehicle; and the formulation is then poured into suitable suppository molds and allowed to solidify.

Ingredients and amounts contemplated by the present invention are shown in the general Formulas A, B and C.

| Ingredient | Quantity in mg |
| --- | --- |
| General Formula A | |
| Calcitonin 25–6,000 I.U. | 0.006–3.0 |
| 0.005–1.0M Acetate buffer, 1–100 μl | |
| Imwitor 308 | 37.5–750 |
| BHA | 0.015–1.5 |
| BHT | 0.015–1.5 |
| Witepsol S 55 or Suppocire AIX or PEG 1,000–8,000 Qs Ad | 1,500* |
| General Formula B | |
| Calcitonin 25–6,000 I.U. | 0.006–3.0 |

| Ingredient | Quantity in mg |
|---|---|
| 1–100 µl per gram of suppository base of: 1 to 32% w/w gelatin solution hydrolized in 0.9% w/w sodium chloride or purified water; pH adjusted to 2.0 to 8.0 with HCl or NaOH. | |
| Imwitor 308 | 37.5–750 |
| BHA | 0.015–1.5 |
| BHT | 0.015–1.5 |
| Witepsol S 55 or Suppocire AIX or PEG 1,000–8,000 Qs Ad | 1,500* |

*While 1,500 mg quantity suppository units are illustrated in General Formula A, B and C, the quantity per unit may be in the range of 500 mg to 5,000 mg.

Preparative examples and typical formulations are set forth below. However, it is to be understood that these examples are given by way of illustration only and are not to be construed as limiting the invention either in spirit or in scope as many modifications will be apparent to those skilled in the art.

EXAMPLE 1

Imwitor 308 (promoter) is melted with Witepsol S 55 base at approximately 45° C. The antioxidants, BHA and BHT, are added and dissolved. The melted mixture is then allowed to cool to a slightly thicker mass. Calcitonin (powder) is dissolved in 0.1 M acetate buffer (pH 4.0) to contain 25 to 6,000 I.U. of salmon calcitonin in 37.5 µl f the solution. The calcitonin solution is added to the blended base and mixed. The mixture is poured into suppository molds and allowed to solidify.

EXAMPLE 2

Imwitor 308 (promoter) is melted with Suppocire AIX base at approximately 45° C. The antioxidants, BHA and BHT, are added and dissolved. The melted mixture is then allowed to cool to a slightly thicker mass. Calcitonin powder is dissolved in 0.1 M acetate buffer (pH 4.0) to contain the desired calcitonin potency in 37.5 µl of the solution The calcitonin solution is added to the blended base and mixed The mixture is poured into suppository molds and allowed to solidify.

EXAMPLE 3

Imwitor 308 (promoter) is melted with PEG 1450 base at approximately 50° C. The antioxidants, BHA and BHT, are added and dissolved. The melted mixture is then allowed to cool to a slightly thicker mass. Calcitonin powder is dissolved in 1–32% gelatin/0.9% sodium chloride solution (pH 3.2) to contain the desired I.U. of calcitonin in 37.5 µl of the solution The calcitonin solution is added to the blended base and mixed The mixture is poured into suppository molds and allowed to solidify.

EXAMPLE 4

Imwitor 308 (promoter) is melted with Witepsol E 75 or Suppocire AIX base at approximately 50° C. The antioxidants, BHA and BHT, are added and dissolved. The melted mixture is then allowed to cool to a slightly thicker mass. Calcitonin, as a calcitonin-mannitol lyophilized powder mixture, is added to the suppository vehicle above and suspended uniformly. The suspension is poured into suppository molds and allowed to solidify.

EXAMPLE 5

| Ingredient | Quantity |
|---|---|
| SCT 45 I.U. in 37.5 µl of a 0.1M acetate buffer (pH 4.0) | 0.025 mg |
| Imwitor 308 | 75 mg |
| BHA | 0.15 mg |
| BHT | 0.15 mg |
| Witepsol S 55 QS | 1500 mg |

EXAMPLE 6

| Ingredient | Quantity |
|---|---|
| SCT 500 I.U. in 37.5 µl of a 0.1M acetate buffer (pH 4.0) | 0.1 mg |
| Imwitor 308 | 100 mg |
| BHA | 0.15 mg |
| BHT | 0.15 mg |
| Suppocire AIX QS | 1500 mg |

EXAMPLE 7

| Ingredient | Quantity |
|---|---|
| SCT 5,000 I.U. in 37.5 µl of a 0.1M acetate buffer (pH 4.0) | 0.050 mg |
| Imwitor 308 | 700 mg |
| BHA | 0.15 mg |
| BHT | 0.15 mg |
| Witepsol S 55 QS | 1500 mg |

EXAMPLE 8

| Ingredient | Quantity |
|---|---|
| SCT 2,000 I.U. | 0.075 mg |
| Mannitol, USP | 75 mg |
| Imwitor 308 | 75 mg |
| BHA | 0.15 mg |
| BHT | 0.15 mg |
| Suppocire AIX QS Ad | 1500 mg |

EXAMPLE 9

| Ingredient | Quantity |
|---|---|
| SCT 400 I.U. | 0.045 mg |
| Mannitol, USP | 225 mg |
| Imwitor 308 | 750 mg |
| BHA | 0.15 mg |
| BHT | 0.15 mg |
| Witepsol E 75 QS Ad | 1500 mg |

EXAMPLE 10

| Ingredient | Quantity |
|---|---|
| SCT 100 I.U. | 0.1 mg |
| Mannitol, USP | 250 mg |
| Imwitor 308 | 500 mg |
| BHA | 0.15 mg |
| BHT | 0.15 mg |
| Suppocire AIX QS Ad | 1500 mg |

EXAMPLE 11

| Ingredient | Quantity |
| --- | --- |
| Calcitonin* in a 20% solution of gelatin hydrolized in 0.9% sodium chloride vehicle, pH adjusted to 3.2 with HCl, 25 μl/g suppository base | 0.1 mg |
| Imwitor 308 | 600 mg |
| BHA | 0.15 mg |
| BHT | 0.15 mg |
| Suppocire AIX QS Ad | 1500 mg |

*1,7-Di-Alanine, 8-glycine, Des-19-Leucine Calcitonin

EXAMPLE 12

| Ingredient | Quantity |
| --- | --- |
| Bovine Calcitonin 400 I.U. in a 32% solution of gelatin hydrolized in purified water vehicle, pH adjusted to 3.2 with HCl, 25 μl/g suppository base | 0.1 mg |
| Imwitor 308 | 75 mg |
| BHA | 0.15 mg |
| BHT | 0.15 mg |
| Suppocire AIX QS Ad | 1500 mg |

EXAMPLE 13

| Ingredient | Quantity |
| --- | --- |
| Calcitonin* in a 10% solution of gelatin hydrolized in 0.9% sodium chloride vehicle, pH adjusted to 3.2 with HCl, 25 μl/g suppository base | 0.1 mg |
| Imwitor 308 | 750 mg |
| BHA | 0.15 mg |
| BHT | 0.15 mg |
| Witepsol S 55 | 1500 mg |

*N-α-Propionyl, 1,7-Di-Alanine, Des-19-Leucine Calcitonin

Suppository formulations of the present invention were tested for hypocalcemic effect according to the following procedure:

Non-promoter and promoter containing salmon calcitonin suppositories were administered rectally into rats and the rectums were sealed to avoid expulsion of the suppositories. Blood samples were analyzed for serum calcium levels at base line, 1, 2, 3 and 4 hours and percent serum calcium level depressions from base line values were calculated and expressed as hypocalcemic response. Reduction of serum calcium levels from base line is a measure of salmon calcitonin activity.

Results obtained are illustrated in Table I. The formulation used is that described in Example 5 with varying amounts of Imwitor 308.

TABLE I

Effect of Promoter (Imwitor 308) in Rectally Administered SCT Suppository to Rats

| Imwitor % in Suppository | % Hypocalcemic Effect (Post Administration) | | | |
| --- | --- | --- | --- | --- |
| | 1 Hour | 2 Hour | 3 Hour | 4 Hour |
| 0 | 19 | 18 | 11 | 9 |
| 2.5 | 23 | 16 | 3 | 2 |
| 5.0 | 28 | 25 | 15 | 8 |
| 10.0 | 26 | 34 | 38 | 32 |
| 25.0 | 26 | 34 | 35 | 34 |
| 50.0 | 28 | 35 | 37 | 35 |

While only certain embodiments of our invention have been described in specific detail, it will be apparent to those skilled in the art that many other specific embodiments may be practiced and many changes may be made all within the spirit of the invention and the scope of the appended claims.

What we claim is:

1. A suppository composition for rectal or vaginal administration comprising: from about 0.0004% w/w to about 0.200% w/w of a polypeptide having calcitonin activity (as hereinbefore defined); from about 2.5% w/w to about 50.0% w/w of caprylic acid monoglyceride; and suppository base selected from the group consisting of mixtures of polyethylene glycols or mixtures of mono-, di- and triglycerides of $C_{10}$ to $C_{20}$ chain length.

2. The suppository composition of claim 1 wherein said polypeptide is salmon calcitonin.

3. The suppository composition of claim 1 wherein said polypeptide is an analog of salmon calcitonin.

4. The suppository composition of claim 1 wherein said polypeptide is selected from the group consisting of eel, bovin, porcine, ovine, rat, chicken, and human calcitonins.

5. The suppository composition of claim 1 wherein said polypeptide is obtained from natural sources.

6. The suppository composition of claim 1 wherein said polypeptide is obtained by a synthetic route.

7. The suppository composition of claim 1 wherein said polypeptide is selected from the group consisting about 10,000 international units per mg of polypeptide.

8. A method for enhancing absorption, through the rectal or vaginal mucosal membranes, of a polypeptide having calcitonin activity comprising: adding from about 2.5% w/w to about 50.0% w/w of caprylic acid monoglyceride to a composition comprising 0.0004% w/w to 0.200% w/w of a polypeptide having calcitonin activity and a pharmaceutically acceptable suppository vehicle in a quantity sufficient to make weight.

9. A method for the treatment of a patient suffering from diseases of hyperparathyroidism, idiopathic hypercalcemia of infancy, Paget's disease, vitamin D intoxication, or osteolytic bone metastases, said diseases characterized by hypercalcemia and high phosphate concentrations in the blood of said patient comprising: administering to said patient in need of such treatment to effect control of at least one of said diseases an effective amount of the composition of claim 1.

10. A suppository composition for rectal or vaginal administration comprising: from about 0.005% w/w to about 0.05% w/w of a polypeptide having calcitonin activity; from about 10% w/w to about 40% w/w of a caprylic acid monoglyceride; and a pharmaceutically acceptable suppository vehicle in a quantity to make weight.

11. The suppository composition of claim 10 wherein said polypeptide is [N-alpha-X, 1,7 Di-Alanine (8-Y) Des-19-Leucine]) calcitonin, wherein X is H, free amino or acyl-amino wherein acyl is derived from a carboxylic acid having 1-10 carbon atoms, L-lactic acid or half amide of malonic, succinic, glutaric, or adipic acids; and Y is L-valine, glycine, L-methionine, L-alanine, L-leucine or L-isoleucine.

12. The suppository composition of claim 10 wherein said polypeptide is: [N-alpha-X, 1,7-Di Alanine, Des-19-Leucine] calcitonin, wherein X is an acyl derived from carboxylic acid having 1-5 carbon atoms.

13. THe suppository composition of claim 10 wherein said polypeptide is:

H—Cys—Ser—Leu—Ser—Thr—Cys—Val—Leu—Gly—
—Lys—Leu—Ser—Gln—Glu—Leu—His—Lys—Leu—Gln—
—Thr—Tyr—Pro—Arg—Thr—Asn—Thr—Gly—Ser—Gly—
—Thr—Pro—NH₂.

14. The suppository composition of claim 10 wherein said polypeptide is:

Cys—Ser—Asn—Leu—Ser—Thr—Cys—Val—Leu—Gly—
Lys—Leu—Ser—Gln—Glu—Ala—His—Lys—Leu—Gln—
Thr—Tyr—Pro—Arg—Thr—Asn—Thr—Gly—Ser—Gly—
Thr—Pro—NH₂ (Salmon).

15. The suppository composition of claim 10 wherein said polypeptide is:

H—Cys—Asn—Leu—Ser—Thr—Cys—Gly—Leu—
Gly—Lys—Leu—Ser—Gln—Glu—Leu—His—
Lys—Leu—Gln—Thr—Pro—Arg—Thr—Asn—
Thr—Gly—Ser—Gly—Thr—Pro—NH₂ (Salmon).

16. The suppository composition of claim 10 wherein said polypeptide is:

Cys—Ser—Asn—Leu—Ser—Thr—Cys—Val—Leu—Gly—
Lys—Leu—Gln—Glu—Leu—His—Lys—Leu—Gln—
Thr—Tyr—Pro—Arg—Thr—Asn—Thr—Gly—Ser—
Gly—Thr—Pro—NH₂.

17. The suppository composition of claim 10 wherein said polypeptide is:

Cys—Ser—Asn—Leu—Ser—Thr—Cys—Val—Leu—Gly—
Lys—Leu—Ser—Gln—Glu—Leu—His—Lys—Leu—Gln—
Tyr—Pro—Arg—Thr—Asn—Thr—Gly—Ser—Gly—Thr—
Pro—NH₂ (Salmon).

18. The suppository composition of claim 10 wherein said polypeptide is:

Cys—Gly—Ser—Leu—Ser—Thr—Cys—Gly—Leu—Gly—
Lys—Leu—Ser—Gln—Glu—Leu—His—Lys—Leu—Gln—
Thr—Pro—Arg—Thr—Asn—Thr—Gly—Ser—Gly—Thr—
Pro—NH₂.

19. The suppository composition of claim 10 wherein said polypeptide is:

Cys—Ser—Asn—Ser—Thr—Cys—Val—Leu—Gly—Lys—
—Leu—Ser—Gln—Glu—Leu—His—Lys—Leu—Gln—Thr—
—Tyr—Pro—Arg—Thr—Asn—Thr—Gly—Ser—Gly—Thr—
—Pro—NH₂ (Salmon).

20. The suppository composition of claim 10 wherein said polypeptide is:

Cys—Ser—Asn—Leu—Ser—Thr—Cys—Val—Leu—Gly—
Lys—Leu—Ser—Gln—Glu—Leu—His—Lys—Leu—
Gln—Thr—Tyr—Pro—NH₂.

21. The suppository composition of claim 10 wherein said polypeptide is:

Bmp—Ser—Asn—Leu—Ser—Thr—Cys—Gly—Leu—Gly—
Lys—Leu—Ser—Gln—Glu—Leu—His—Lys—Leu—Gln—
Thr—Tyr—Pro—Arg—Thr—Asn—Thr—Gly—Ser—Gly—
Thr—Pro—NH₂ (Salmon).

22. The suppository composition of claim 10 wherein said polypeptide is:
Ala-Ser-Asn-Leu-Ser-Thr-Ala-Val-Leu-Cly-Lys-
Leu-Ser-Gln-Glu-Ala-His-Lys-Leu-Gln-Thr-Tyr-
Pro-Arg-Thr-Asn-Thr-Gly-Ser-Gly-Thr-Pro-Nh₂.

23. The suppository composition of claim 10 wherein said polypeptide is:

Cys—Ser—Asn—Leu—Ser—Thr—Cys—Met—Leu—
Gly—Lys—Leu—Ser—Gln—Glu—Leu—His—Lys—
Leu—Gln—Thr—Tyr—Pro—Arg—Thr—Asn—Thr—
Gly—Ser—Gly—Thr—Pro—NH₂.

24. The suppository composition of claim 10 wherein said polypeptide is:

Cys—Leu—Ser—Thr—Cys—Val—Leu—Gly—Lys—
Leu—Ser—Gln—Glu—Leu—His—Lys—Leu—Gln—
Thr—Tyr—Pro—Arg—Thr—Asn—Thr—Gly—Ser—
Gly—Thr—Pro—NH₂.

25. The suppository composition of claim 10 wherein said polypeptide is:

$R_1$ \qquad\qquad $R_2$
Cys—Ser—Asn—Leu—Ser—Ser—Cys—Val—Leu—Gly—Lys—
Lys—Leu—Ser—Glu—Glu—Leu—His—Lys—Gln—Thr—Tyr—
Pro—Arg—Thr—Asn—Thr—Gly—Ser—Gly—Thr—Pro—NH₂;

where $R_1$ is S-n-alkyl, Cys or H and $R_2$ is S-n-alkyl or H, $R_1$ being S-n-alkyl, Cys or H when $R_2$ is H and $R_2$ being S-n-alkyl or H when $R_1$ is H.

26. The suppository composition of claim 10 wherein said polypeptide is:

Cys—Ser—Asn—Leu—Ser—Ser—Cys—Val—Leu—Gly—
Lys—Leu—Ser—Gln—Glu—Leu—His—Lys—Gln—Thr—
Tyr—Pro—Arg—Thr—Asn—Thr—Gly—Ser—Gly—Thr—
Pro—NH₂.

27. The suppository composition of claim 10 wherein said polypeptide is:

SCH₂NH—C(O)—CH₃
|
Cys—Ser—Asn—Leu—Ser—Thr—Ala—Val—Leu—Gly—

-continued

Lys—Leu—Ser—Gln—Glu—Leu—His—Lys—Leu—Gln—

Thr—Tyr—Pro—Arg—Thr—Asn—Thr—Gly—Ser—Gly—

Thr—Pro—NH₂.

28. The suppository composition of claim 10 wherein said polypeptide is:

⌐Cys—Ser—Asn—Leu—Ser—Thr—Cys⌐—Val—Leu—

Gly—Lys—Leu—Ser—Gln—Glu—Leu—His—Lys—

Gln—Thr—Tyr—Pro—Arg—Thr—Asn—Thr—Gly—

Ser—Gly—Thr—Pro—NH₂.

29. The suppository composition of claim 10 wherein said polypeptide is:

$$\text{S—CH}_2\text{—NH—}\overset{\overset{O}{\|}}{\text{C}}\text{—CH}_3$$
H—Cys—Ser—Asn—Leu—Ser—Thr—

$$\text{S—CH}_2\text{—NH—}\overset{\overset{O}{\|}}{\text{C}}\text{—CH}_3$$
Cys—Val—Leu—Gly—Lys—Leu—Ser—Gln—Glu—Leu—

His—Lys—Leu—Gln—Thr—Tyr—Pro—Arg—Thr—Asn—

Thr—Gly—Ser—Gly—Thr—Pro—NH₂.

30. The suppository composition of claim 10 wherein said polypeptide is:

⌐Cys—Ser—Asn—Leu—Ser—Thr—Cys⌐—Gly—Leu—Gly—

Lys—Leu—Ser—Gln—Glu—Leu—His—Lys—Gln—

Thr—Tyr—Pro—Arg—Thr—Asn—Thr—Gly—Ser—

Gly—Thr—Pro—NH₂ (Salmon).

31. The suppository composition of claim 10 wherein said polypeptide is:

⌐Cys—Ser—Asn—Leu—Ser—Thr—Cys⌐—Val—Leu—Gly—

Lys—Leu—Ser—Gln—Glu—His—Lys—Leu—Gln—

Thr—Tyr—Pro—Arg—Thr—Asn—Thr—Gly—Ser—

Gly—Thr—Pro—NH₂ (Salmon).

32. The suppository composition of claim 10 wherein said polypeptide is:

⌐H—Cys—Ser—Asn—Leu—Ser—Thr—Cys⌐—Val—Leu—

Gly—Lys—Leu—Ser—Gln—Glu—Leu—His—Lys—Leu—

Gln—Thr—Leu—Pro—Arg—Thr—Asn—Thr—Gly—Ser—

Gly—Thr—Pro—NH₂ (Salmon).

33. The suppository composition of claim 10 wherein said polypeptide is:

⌐H—Cys—Ser—Asn—Leu—Ser—Thr—Cys⌐—Gly—Leu—

Gly—Lys—Leu—Ser—Gln—Glu—Leu—His—Lys—Leu—

Gln—Thr—Tyr—Pro—Arg—Thr—Asn—Thr—Gly—Ser—

Gly—Thr—Pro—NH₂.

34. The suppository composition of claim 10 wherein said polypeptide is:

⌐H—Cys—Ser—Asn—Leu—Ser—Thr—Cys⌐—Gly—Leu—

Gly—Lys—Leu—Ser—Gln—Glu—Leu—His—Lys—Leu—

Gln—Thr—Tyr—Pro-D-Arg—Thr—Asn—Thr—Gly—Ser—

Gly—Thr—Pro—NH₂ (Salmon).

35. The suppository composition of claim 10 wherein said polypeptide is:

⌐H—Cys—Ser—Asn—Leu—Ser—Thr—Cys⌐—Val—Leu—

Gly—Lys—Leu—Ser—Gln—Glu—Leu—His—Lys—Leu—

Gln—Tyr—Tyr—Pro—Arg—Thr—Asn—Thr—Gly—Ser—

Gly—Thr—Pro—NH₂ (Salmon).

36. The suppository composition of claim 10 wherein said polypeptide is:

⌐H—Cys—Ser—Asn—Leu—Ser—Thr—Cys⌐—Val—Leu—

Gly—Lys—Leu—Ser—Gln—Glu—Leu—His—Lys—Leu—

Gln—Thr—Tyr—Pro-D-Arg—Thr—Asn—Thr—Gly—Ser—

Gly—Thr—Pro—NH₂ (Salmon).

37. The suppository composition of claim 10 wherein said polypeptide is:

⌐Y—Cys—Ser—Asn—Leu—Ser—Thr—Cys⌐—Val—Leu—
   1    2    3    4    5    6    7    8    9

X                              X
     |                              |
Gly—Lys—Leu—Ser—Gln—Glu—Leu—His—Lys—Leu—
10  11   12  13   14   15  16   17  18   19

X
                    |
Gln—Thr—Tyr—Pro—Arg—Thr—Asn—Thr—Gly—Ser—
20   21  22   23  24   25  26   27  28  29

Gly—Thr—Pro—NH₂
30   31  32 wherein Y is N(a) decanoyl and X is N(e) decanoyl.

38. The suppository composition of claim 10 wherein said polypeptide is:

H₂N—Ala—Ser—Asn—Leu—Ser—Thr—Ala—Gly—Leu—
       1                   5

Gly—Lys—Leu—Ser—Gln—Glu—Leu—His—Lys—Gln—
    10                  15

Thr—Tyr—Pro—Arg—Thr—Asn—Thr—Gly—Ser—Gly—
    20                  25

Thr—Pro—(C=O)—NH₂.
    30

39. The suppository composition of claim 10 wherein said polypeptide is:

CH₃—CH₂—(C=O)—Hn—

Ala—Ser—Asn—Leu—Ser—Thr—Ala—Val—Leu—Gly—
 1                 5                    10

Lys—Leu—Ser—Gln—Glu—Leu—His—Lys—Gln—Thr—
                15                    20

Tyr—Pro—Arg—Thr—Asn—Thr—Gly—Ser—Gly—Thr—
              25                    30

Pro—(C=O)—NH₂.

* * * * *